United States Patent
Bower et al.

(10) Patent No.: US 10,429,310 B2
(45) Date of Patent: Oct. 1, 2019

(54) APPARATUS AND METHOD FOR SENSING A PARAMETER

(71) Applicant: Nokia Technologies Oy, Espoo (FI)

(72) Inventors: Chris Bower, Cambridge (GB); Darryl Cotton, St. Ives Cambridgeshire (GB); Mark Allen, Great Cambourne (GB); Michael Astley, Cambridge (GB); Joseph Bottomley, Cambridge (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 73 days.

(21) Appl. No.: 15/500,212

(22) PCT Filed: Jul. 30, 2015

(86) PCT No.: PCT/FI2015/050514
§ 371 (c)(1),
(2) Date: Jan. 30, 2017

(87) PCT Pub. No.: WO2016/016513
PCT Pub. Date: Feb. 4, 2016

(65) Prior Publication Data
US 2017/0350822 A1    Dec. 7, 2017

(30) Foreign Application Priority Data
Aug. 1, 2014 (EP) .................................... 14179588

(51) Int. Cl.
*G01N 21/78* (2006.01)
*G01N 27/04* (2006.01)
(Continued)

(52) U.S. Cl.
CPC ............. *G01N 21/78* (2013.01); *G01N 27/04* (2013.01); *G01N 27/125* (2013.01); *G06F 3/044* (2013.01)

(58) Field of Classification Search
CPC ........ G01N 21/78; G01N 21/77; G01N 21/75; G01N 27/04; G01N 27/02; G01N 27/00
(Continued)

(56) References Cited

U.S. PATENT DOCUMENTS 8,267,576 B2    9/2012    Haarer et al.
2007/0203650 A1  8/2007    Jensen et al.
(Continued)

FOREIGN PATENT DOCUMENTS

CN    103020554    4/2013
CN    104123644    10/2014
(Continued)

OTHER PUBLICATIONS

Turke, Alexander et al, English Machine Translation of DE 10 2013 103 127 B3 of ABST, DESC and Claim, obtained on Jul. 26, 2018, pp. 1-37. (Year: 2018).*
(Continued)

*Primary Examiner* — Christine T Mui
(74) *Attorney, Agent, or Firm* — Alston & Bird LLP

(57) ABSTRACT

An apparatus and method comprising: a plurality of sensor elements wherein the sensor elements are configured to be actuated in response to exposure to a parameter and the apparatus is configured to record when each of the sensor elements are actuated wherein: the plurality of sensor elements comprises at least a first subset of sensor elements and at least a second subset of sensor elements where the first subset of sensor elements are actuated in response to a first level of exposure to a parameter and the second subset of sensor elements are actuated in response to a second level of exposure to a parameter.

20 Claims, 8 Drawing Sheets

(51) Int. Cl.
   *G01N 27/12* (2006.01)
   *G01N 27/00* (2006.01)
   *G06F 3/044* (2006.01)

(58) Field of Classification Search
   USPC .................................. 436/2; 422/50, 83, 119
   See application file for complete search history.

(56) References Cited

U.S. PATENT DOCUMENTS

| | | |
|---|---|---|
| 2009/0167699 A1 | 7/2009 | Rosenblatt et al. |
| 2011/0029413 A1 | 2/2011 | Ben-Tzur et al. |
| 2011/0253789 A1 | 10/2011 | Thiele et al. |
| 2011/0260842 A1 | 10/2011 | Colley |
| 2012/0125993 A1 | 5/2012 | Thiele et al. |
| 2013/0112755 A1 | 5/2013 | Allen et al. |
| 2013/0176252 A1 | 7/2013 | Frojdh |
| 2013/0271265 A1 | 10/2013 | Finn |
| 2013/0320080 A1 | 12/2013 | Olson et al. |
| 2014/0009291 A1 | 1/2014 | Requist et al. |
| 2014/0011286 A1 | 1/2014 | Potyrailo et al. |
| 2014/0013865 A1 | 1/2014 | White et al. |
| 2014/0055244 A1 | 2/2014 | Burchell et al. |
| 2014/0079932 A1 | 3/2014 | Aksay et al. |
| 2014/0327645 A1 | 11/2014 | Matthews et al. |
| 2015/0073983 A1 | 3/2015 | Bartenstein et al. |
| 2016/0070418 A1 | 3/2016 | Ogata |

FOREIGN PATENT DOCUMENTS

| | | |
|---|---|---|
| DE | 103430187 | 12/2013 |
| DE | 102013103127 B3 | 5/2014 |
| EP | 2077484 | 7/2009 |
| EP | 2535840 A1 | 12/2012 |
| EP | 2535841 | 12/2012 |
| JP | 2006/164164 A | 6/2006 |
| JP | 2010/039896 A | 2/2010 |
| WO | WO 2008/050468 | 2/2010 |
| WO | 2011/053297 A1 | 5/2011 |
| WO | 2012/028748 A1 | 3/2012 |
| WO | 2012/172047 A1 | 12/2012 |
| WO | 2013/144788 A1 | 10/2013 |
| WO | WO 2014/174636 A1 | 10/2014 |

OTHER PUBLICATIONS office action for corresponding European Patent Application No. 14179576.5, dated Mar. 31, 2017, 4 pages.
Non-Final Office action for corresponding U.S. Appl. No. 15/329,715, dated Sep. 11, 2017, 7 pages.
Office action for corresponding European Patent Application No. 14179588.0, dated Oct. 12, 2017, 8 pages.
"Thinfilm", Thinfilm, Retrieved on Jan. 25, 2017, Webpage available at : http://thinfilm.no/.
"Touchcode", T-ink, Retrieved on Jan. 18, 2017, Webpage available at : http://www.t-ink.com/products/touchcode/.
Jung et al., "All-Printed and Roll-To-Roll-Printable 13.56-MHz-Operated 1-bit RF Tag on Plastic Foils", IEEE Transactions on Electron Devices, vol. 57, No. 3, Mar. 2010, pp. 571-580.
Zirkl et al., "An All-Printed Ferroelectric Active Matrix Sensor Network Based on Only Five Functional Materials Forming a Touchless Control Interface", Advanced Materials, vol. 23, No. 18, 2011, pp. 2069-2074.
Kim et al., "Electrolyte-Gated Transistors for Organic and Printed Electronics", Advanced Materials, vol. 25, 2013, pp. 1822-1846.
Allen et al., "Contactless Read-Out of Printed Memory", Microelectronic Engineering, vol. 88, No. 9, Sep. 2011, pp. 2941-2945.
Leppaniemi et al., "Roll-To-Roll Printed Resistive WORM Memory on a Flexible Substrate", Nanotechnology, vol. 23, No. 30, 2012, pp. 1-12.
Yu et al., "TUIC: Enabling Tangible Interaction on Capacitive Multi-Touch Display", Proceedings of the SIGCHI Conference on Human Factors in Computing Systems, May 7-12, 2011, pp. 2995-3004.
"Sense and Sensor-Bility: Access Mobile Device Sensors With JavaScript", Mobiforge, Retrieved on Jan. 25, 2017, Webpage available at : https://mobiforge.com/design-development/sense-and-sensor-bility-access-mobile-device-sensors-with-javascript.
Saxena et al., "Vibrate-To-Unlock: Mobile Phone Assisted User Authentication To Multiple Personal RFID Tags", IEEE International Conference on Pervasive Computing and Communications (PerCom), Mar. 21-25, 2011, pp. 181-188.
Extended European Search Report for corresponding European Patent Application No. 14179576.5, dated Jan. 21, 2015, 7 pages.
Extended European Search Report for corresponding European Patent Application No. 14179588.0, dated Feb. 2, 2015, 11 pages.
International Search Report and Written Opinion for corresponding Patent Cooperation Treaty Application No. PCT/FI2015/050504, dated Sep. 28, 2015, 13 pages.
International Search Report and Written Opinion for corresponding Patent Cooperation Treaty Application No. PCT/FI2015/050514, dated Oct. 26, 2015, 14 pages.
Zhang et al., "Humidity-Sensing Properties of Chemically Reduced Graphene Oxide/Polymer Nanocomposite Film Sensor Based on Layer-By-Layer Nano Self-Assembly", Sensors and Actuators B: Chemical, vol. 197, Jul. 5, 2014, pp. 66-72.
"Temp-Plate Irreversible Temperature Recording Labels", Wahl Instruments Inc., Retrieved on Jan. 20, 2017, Webpage available at : http://www.palmerwahl.com/pdfs/TempPiate/.
Lipatov et al., "Highly Selective Gas Sensor Arrays Based on Thermally Reduced Graphene Oxide", Nanoscale, vol. 5, No. 13, Apr. 12, 2013, pp. 5426-5434.
Office Action for corresponding Japanese Application No. 2017-505092 dated Feb. 27, 2018.
Office Action for Japanese Application No. 2017-505092 dated Sep. 27, 2018.
Office Action for U.S. Appl. No. 15/329,715 dated May 11, 2018, 6 pages.
V. Kayashtha et al., "Ultrafast Integrated Humidity and Temperature Sensor Based on Carbon Nanotubes, and a Sensor Controller System", (2014), [online], [2014], retrieved from the internet <URL:https://briefs.techconnect.org/wp-content/volumes/Nanotech2014v1/pdf/722.pdf, (4 pages).
Office Action for Japanese Application No. 2017-505092 dated Mar. 19, 2019.
Office Action for Chinese Application No. 201580053401.6 dated Jun. 5, 2019.

* cited by examiner

APPARATUS AND METHOD FOR SENSING A PARAMETER

CROSS-REFERENCE TO RELATED APPLICATIONS

This application is a national phase application filed under 35 U.S.C. § 371 of International Application No. PCT/FI2015/050514 filed Jul. 30, 2015 which claims priority benefit from EP Application No. 14179588.0, filed Aug. 1, 2014.

TECHNOLOGICAL FIELD

Examples of the disclosure relate to an apparatus and method for sensing a parameter. In particular, they relate to an apparatus and method for sensing a parameter and recording when a level of exposure to the parameter is detected.

BACKGROUND

Apparatus such as smart tags or labels that can be used in supply chain management of goods are known. Such apparatus may be used to monitor the exposure of sensitive goods to environmental conditions such as temperature variations, ultra violet (UV) radiation, humidity or any other parameters.

The goods may comprise, for example, food products or medicines which may have storage conditions that must be met to ensure they are maintained in a satisfactory condition. For example, when transporting vaccines or other medicines, it is important that they do not get exposed to elevated temperatures which may degrade the efficacy of the medicine.

In order to provide low cost smart tags and labels such apparatus may use chemical or physical processes to provide a visible colour change to a portion of the smart tag or label. The user can then determine whether or not the goods are still in a satisfactory condition by looking at the colour of the label. This enables the smart tags and labels to be simple devices without any electronic components or moving parts. However such smart tags and labels only provide a limited amount of information to the user.

It is advantageous to provide an apparatus which may be configured to provide detailed information about the environmental conditions that the goods have been exposed to.

BRIEF SUMMARY

According to various, but not necessarily all examples of the disclosure, there may be provided an apparatus comprising: a plurality of sensor elements wherein the sensor elements are configured to be actuated in response to exposure to a parameter and the apparatus is configured to record when each of the sensor elements are actuated wherein: the plurality of sensor elements comprises at least a first subset of sensor elements and at least a second subset of sensor elements where the first subset of sensor elements are actuated in response to a first level of exposure to a parameter and the second subset of sensor elements are actuated in response to a second level of exposure to a parameter.

In some examples the plurality of sensor elements may be configured so that a sensing material within the first subset of sensor elements is configured to detect a first level of exposure to a parameter and a sensing material within the second subset of sensor elements is configured to detect a second level of exposure to a parameter.

In some examples the sensing material may comprise graphene oxide. The graphene oxide may be configured to be reduced in response to exposure to a parameter.

In some examples the first subset of sensing elements may comprise a sensing material having a first width and the second subset of sensing elements may comprise a sensing material having a second width.

In some examples the first subset of sensing elements may comprise a first barrier layer with a first level of permeability to the parameter and the second subset of sensing elements may comprise a second barrier layer with a second level of permeability to the parameter.

In some examples the plurality of sensing elements may comprise a getter material configured to control the sensitivity of the sensor elements to the parameter.

In some examples at least one of the plurality of sensor elements may comprise a portion of sensing material and an irreversible memory portion. The portion of sensing material may be reversible such that changes to the sensing material caused by the exposure to the parameter may be reversed. The apparatus may comprise a plurality of sensor elements comprising a portion of sensing material and an irreversible memory portion wherein each of the portions of sensing material are identical but each of the irreversible memory portions are different.

In some examples the plurality of sensor elements may comprise electrodes to enable the data obtained by the sensor elements to be read out from the apparatus using a capacitive touch display. In some examples at least one reference electrode may be configured to enable relative positions of sensor elements to be determined. In some examples the apparatus may be configured to enable data read out from the apparatus to be displayed on the capacitive touch display.

In some examples the sensor elements may be configured to be activated in response to exposure to at least one of increased temperature, light, humidity.

In some examples more than two subsets of sensor elements may be provided.

According to various, but not necessarily all examples of the disclosure, there may be provided an identification tag comprising an apparatus as described above.

According to various, but not necessarily all examples of the disclosure, there may be provided a method comprising: providing a plurality of sensor elements wherein the sensor elements are configured to be actuated in response to exposure to a parameter and the apparatus is configured to record when each of the sensor elements are actuated; and configuring the plurality of sensor elements such that at least a first subset of sensor elements are actuated in response to a first level of exposure to a parameter and at least a second subset of sensor elements are actuated in response to a second level of exposure to a parameter.

In some examples the plurality of sensor elements may be configured so that a sensing material within the first subset of sensor elements is configured to detect a first level of exposure to a parameter and a sensing material within the second subset of sensor elements is configured to detect a second level of exposure to a parameter.

In some examples the sensing material may comprise graphene oxide. The graphene oxide may be configured to be reduced in response to exposure to a parameter.

In some examples the first subset of sensing elements may comprise a sensing material having a first width and the second subset of sensing elements comprise a sensing material having a second width.

In some examples the method may further comprise providing a first barrier layer with a first level of permeability to the parameter for the first subset of sensing elements and providing a second barrier layer with a second level of permeability to the parameter for the second subset of sensing elements.

In some examples the plurality of sensing elements may comprise a getter material configured to control the sensitivity of the sensor elements to the parameter.

In some examples at least one of the plurality of sensor elements may comprise a portion of sensing material and an irreversible memory portion. In some examples the portion of sensing material may be reversible such that changes to the portion of sensing material caused by the exposure to the parameter may be reversed.

In some examples a plurality of sensor elements comprising a portion of sensing material and an irreversible memory portion may be provided and each of the portions of sensing material may be identical but each of the irreversible memory portions may be different.

In some examples the method may further comprise providing at least one electrode configured to enable the data obtained by the sensor elements to be read out from the apparatus using a capacitive touch screen. In some examples the method may further comprise providing at least one reference electrode configured to enable relative positions of sensor elements to be determined.

In some examples the apparatus may be configured to enable the data read out from the apparatus to be displayed on the display.

In some examples the sensor elements may be configured to be activated in response to exposure to at least one of increased temperature, light, humidity.

In some examples the method may comprise providing more than two subsets of sensor elements.

According to various, but not necessarily all, examples of the disclosure there may be provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

The Figures illustrate an apparatus 1 comprising: a plurality of sensor elements 3 wherein the sensor elements 3 are configured to be actuated in response to exposure to a parameter and the apparatus 1 is configured to record when each of the sensor elements 1 are actuated wherein: the plurality of sensor elements 3 comprises at least a first subset of sensor elements 3 and at least a second subset of sensor elements 3 where the first subset of sensor elements 3 are actuated in response to a first level of exposure to a parameter and the second subset of sensor elements 3 are actuated in response to a second level of exposure to a parameter.

The apparatus 1 may be for sensing exposure to a parameter. The apparatus 1 may be for detecting exposure to a parameter over a period of time and providing a record of the exposure. The apparatus 1 may be attached to goods such as food, medicine, chemical agents or any other suitable product to provide an indication of the history of exposure to a particular parameter for the goods. The apparatus 1 may be provided within an identification tag.

Figure 1:
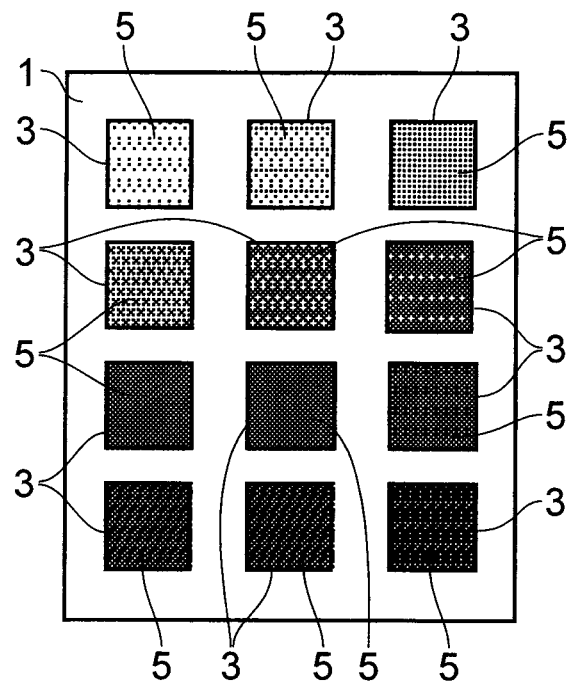
FIG. 1 illustrates an apparatus.

FIG. 1 illustrates an example apparatus 1. The apparatus 1 comprises a plurality of sensor elements 3. Each sensor element 3 comprises a portion of sensing material 5 which may be configured to detect a parameter or combination of parameters. In some examples each of the sensor elements 3 within the apparatus 1 may be configured to detect the same parameter or combinations of parameters. In other examples the apparatus 1 may comprise different groups of sensor elements 3. Different groups of the sensor elements 3 may be configured to detect different parameters or combinations of parameters.

The example apparatus 1 of FIG. 1 comprises twelve sensor elements 3. It is to be appreciated that other numbers of sensor elements 3 could be provided in other examples of the disclosure.

In the example apparatus of FIG. 1 the plurality of sensor elements 3 are arranged in an array on the surface of the apparatus 1. The array comprises a plurality of rows and a plurality of columns. It is to be appreciated that other arrangements of the sensor elements 3 may be used in other examples of the disclosure.

In the example of FIG. 1 each of the sensor elements 3 comprises a square of sensing material 5. It is to be appreciated that other shapes of sensing material 5 may be used in other examples of the disclosure. The shapes that are used may be simple to form using printing techniques.

The sizes of the portions of sensing material 5 may be selected so that the actuation of the sensor elements 3 can be detected. The actuation of the sensor element 3 may comprise a chemical or physical change of the sensing material 5 in response to the detection of a parameter. In some examples the actuation of a sensor element 3 may also comprise triggering a memory element.

In some examples the sizes of the portions of sensing material 5 may be selected so that a change in conductivity of the sensing material 5 can be detected. In the examples of FIG. 1 the portions of sensing material 5 may be 10 mm square regions. It is to be appreciated that other sizes of portions of sensing material 5 may be used in other examples of the disclosure.

The sensing material 5 may comprise any material which may be configured to undergo a physical or chemical change in response to exposure to a parameter or combination of parameters and provide an output indicating that the parameter or combination of parameters have been detected. The parameters which the sensing material 5 may be configured to detect may comprise increased temperature, light, UV light, humidity, chemicals or any other parameter which may be found in the environment of the apparatus 1.

The sensing material 5 may comprise any suitable material such as graphene oxide, graphene, functionalized graphene, polythiopene/iodine combinations or any other suitable material. In examples where graphene oxide is used the sensitivity of the sensor element 3 may be adjusted by modifying the reduction rate of the graphene oxide. The reduction rate may be modified by incorporating a reducing agent such as ascorbic acid, or by increasing the pH or by any other suitable means. The sensing material 5 which is used may depend on the parameter which is to be detected.

The output which indicates that the parameter has been detected may depend on the material which is used as the sensing material 5 and/or the parameter which is to be detected. In some examples the output may comprise a change in colour of the sensing material 5. In such cases when the sensor element 3 is actuated the sensing material 5 may change colour. The user may then be able to see which sensor elements 3 have been actuated by looking at the colours of the sensor elements.

In some examples the output may comprise a change in the physical properties of the sensing material 5. For example, it may comprise a change in the conductivity or other electrical property of the sensing material 5. In such examples the user may determine which of the sensing elements 3 have been activated by applying an electric signal to the apparatus 1 and detecting a change in the electrical properties of the sensing material 5. In some examples, described below, the electric signal may be provided by a capacitive touch screen.

In some examples the sensing material 5 may comprise graphene oxide. The graphene oxide is initially a light yellowish brown colour. When the graphene oxide is exposed to parameters such as increased temperature, humidity or UV light or any combination of these, it converts to reduced graphene oxide. The reduced graphene oxide has an increase in optical density which causes a colour change to a dark grey-black colour. This may enable a user to see which sensing elements 3 have been exposed to the parameters by looking at the colour of the sensing elements 3. The reduced graphene oxide also has a corresponding increase in electrical conductivity. The increased electrical conductivity may be detected by applying an electrical signal to the apparatus 1.

In the example apparatus 1 a plurality of sensor elements 3 are provided. The plurality of sensor elements 3 comprise at least a first subset of sensor elements 3 and at least a second subset of sensor elements 3. The first subset of sensor elements 3 are actuated in response to a first level of exposure to a parameter or combination of parameters and the second subset of sensor elements 3 are actuated in response to a second level of exposure to a parameter or combination of parameters. It is to be appreciated that any number of subsets of sensor elements 3 may be provided. Each subset of sensor elements 3 may be arranged to be actuated in response to a different level of exposure to a parameter or combination of parameters.

In the example of FIG. 1 twelve sensor elements 3 are provided. Each of the sensor elements 3 may be configured to be actuated in response to a different level of exposure to a parameter or combination of parameters. This can be seen by the different colour of each of the portions of sensing material 5 in the apparatus 1 which is represented by shading in FIG. 1. In the example of FIG. 1 the apparatus 1 comprises twelve subsets of sensor elements 3 and each subset comprises one sensor element 3. In other examples some of the subsets may comprise more than one sensor element.

The different subsets of sensor elements 3 may be arranged to be actuated in response to exposure to different levels of a parameter or combinations of parameters. Any suitable method for controlling the sensitivity of the sensor elements 3 may be used. Examples for controlling the sensitivity of the sensor elements 3 are described below.

The apparatus 1 may be configured to record when each of sensor elements is actuated. In some examples when a sensor element 3 is actuated this may cause the sensing material 5 to undergo an irreversible change so that once the change has occurred it cannot be reversed. As different sensing elements 3 have different sensitivities this can provide a detailed record about the level of exposure to a parameter. In other examples the sensor elements 3 may comprise memory portions which may be configured to record when the sensor element 3 is actuated. These may be used with reversible or irreversible sensing material 5.

For instance graphene oxide may be used in a sensing element 3 as both the sensing material 5 and a memory element or may be used in a sensing element with an additional memory element. At high temperatures and humidity graphene oxide irreversibly changes colour, as described above, which allows a user to determine whether or not the apparatus 1 has been exposed to the parameters by looking at the colour of the graphene oxide. Also at high temperatures and humidity graphene oxide irreversibly changes conductivity which allows the actuation of sensor elements 3 to be detected using a capacitive touch screen as described below. At lower temperatures and humidity the changes to the graphene oxide may be reversible. These changes can be recorded by coupling the graphene oxide to an irreversible memory element.

In some examples the apparatus 1 may comprise means for attaching the apparatus 1 to goods or the packaging of goods. For example the apparatus 1 may comprise an adhesive label or any other suitable means which enables the apparatus 1 to be adhered to another item. In other examples the apparatus 1 may be printed directly onto the goods or the packaging of the goods.

Figures 2A, 2B:
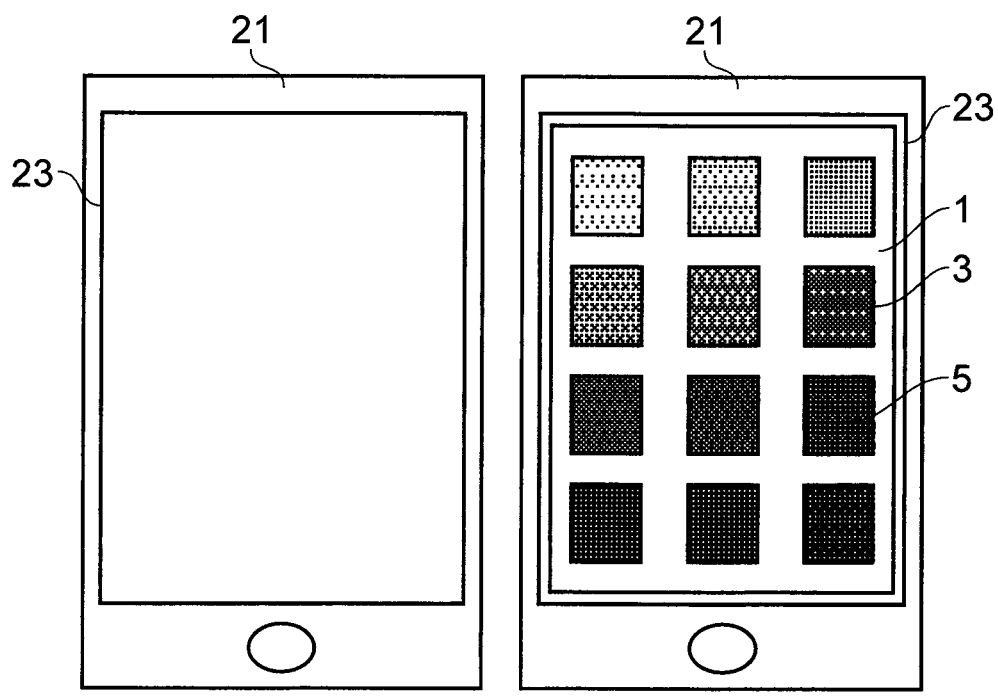
FIGS. 2A and 2B illustrate a capacitive touch display being used to read data from an apparatus.

FIGS. 2A and 2B illustrate an electronic device 21 being used to read data from an example apparatus 1. The apparatus 1 may be as described above in relation to FIG. 1.

FIG. 2A illustrates an example electronic device 21 which may be used to read data from an apparatus 1. The electronic device 21 may be a communication device such as a mobile telephone or tablet computer or any other device 21. The electronic device 21 may be a hand held device in that it may be configured to be held in a user's hand during use.

The electronic device 21 comprises a capacitive touch screen 23. The capacitive touch screen 23 is configured to detect conductive objects which are positioned in proximity to the capacitive touch screen 23. The capacitive touch screen 23 may also be configured to determine the position of the conductive object. The conductive object may comprise a user's finger or one or more of the sensor elements 3 within the apparatus 1.

FIG. 2B illustrates an apparatus 1 positioned on the capacitive touch screen 23. The electronic device 21 may comprise controlling circuitry which may be configured to detect the number of conductive regions on the apparatus 1. In examples where the sensing material 5 comprises graphene oxide the conductive regions will correspond to sensor elements 3 which have been actuated. If a sensor element 3 has not been actuated, the graphene oxide will not be reduced and so the sensor element will not be conductive. The sensor elements 3 which have not been actuated would not be detected by the capacitive touch screen 23.

In some examples the capacitive touch screen 23 may be configured to make a measurement of the capacitance in a region where an actuated sensor element 3 has been detected. The capacitance which is measured may be proportional to the level of exposure to a parameter. For example, where the sensing material 5 comprises graphene oxide the conversion to reduced graphene oxide is proportional to the level of exposure to a parameter such as increased temperature or humidity. As the conductivity of the sensor element 3 is determined by the amount of graphene oxide which has been converted to reduced graphene oxide the measurement of the capacitance may provide detailed information about the level of exposure to parameters. This may enable the apparatus 1 to be used to provide detailed information about the level of exposure to a parameter just by placing the apparatus 1 on a capacitive touch screen.

The electronic device 21 may be configured to control the capacitive touch screen 23 to display the information read out from the apparatus 1. In some examples apparatus 1 may be transparent so that the information displayed on the capacitive touch screen 23 may be viewed through the apparatus 1.

FIGS. 3A to FIG. 12 illustrate example sensor elements 3 which may be provided in examples of the apparatus 1. The sensor elements 3 may be arranged so that different sensor elements 3 have different sensitivities to a parameter or combination of parameters. It is to be appreciated that other sensor elements may be used in other examples of the disclosure.

FIGS. 3A to 3D schematically illustrate some example sensor elements 3 which may be used in example apparatus 1. In the examples of FIGS. 3A to 3D the sensor elements 3 comprise a portion of sensing material 5 and a conductor 31. The conductor 31 is connected to ground. In some examples the ground may be formed by the user touching the conductor 31 so that the body of the user may provide a charge reservoir.

The sensing material 5 in the example sensor elements 3 is configured to detect different levels of exposure to a parameter or combination of parameters. In the examples of FIGS. 3A to 3D the sensing material 5 comprises a channel 35 and a portion 37 adjacent to the conductor 31. The portion 37 adjacent to the conductor 31 may be in electrical contact with the conductor 31. The portion 37 adjacent to the conductor 31 may be in direct electrical contact with the conductor 31 to provide a path for direct current from the portion 37 of sensing material to ground. The portion 37 adjacent to the conductor 31 may be sized and shaped so that when the sensing element is actuated the corresponding change in the conductivity of the portion 37 may be detected.

The channel 35 may be configured so that when the sensing element 3 is exposed to a parameter this causes a change in the sensing material 5 within the channel 35. If the sensing element 3 is exposed to the parameter for a long enough time the change in the sensing material 5 will reach the portion 37 in electrical contact with the conductor 31.

In the examples of FIGS. 3A to 3D a barrier layer 33 is provided overlaying a portion of the sensing material 5. The barrier layer 33 may comprise any material which may be configured to be impermeable to the parameter which is to be detected. In the examples of FIGS. 3A to 3D the barrier layer 33 is provided overlaying the portion 37 of the sensing material 5 which is adjacent to the conductor 31.

In the examples of FIGS. 3A to 3D the sensitivity of the sensor element 3 is controlled by controlling the cross sectional area or the distance from the closest exposed section of the channel 35 to the grounded conductive portion 31.

Figure 3A:
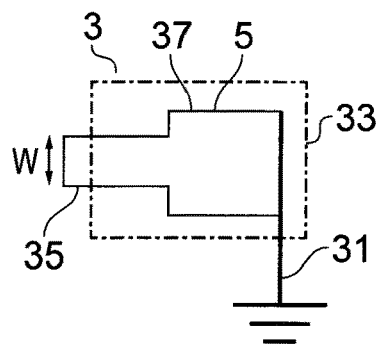
FIGS. 3A to 3D illustrate example sensor elements.
Figure 3C:
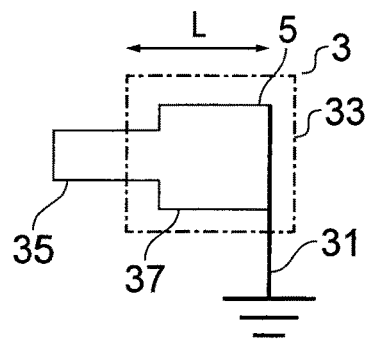
Figure 3B:
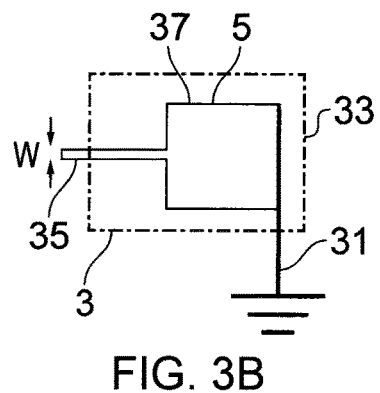

In the examples of FIGS. 3A and 3B the sensitivity of the sensor element 3 is controlled by controlling the width w of the channel 35. The sensor element 3 of FIG. 3A has a wide channel 35 and the sensor element 3 of FIG. 3B has a narrow channel 35. Only two different channel widths are shown in FIGS. 3A and 3B however it is to be appreciated that any number of different channel widths may be used in examples of the disclosure.

In examples where the sensing material 5 comprises graphene oxide decreasing the width of the channel 35 may increase the time taken for the reduction of the graphene oxide to reach the portion 37 of the sensing material 5 which is adjacent to the conductor 31. In such examples the sensing elements 3 with the narrow channel 35 widths would be actuated after a higher level of exposure to the parameters.

Figure 3D:
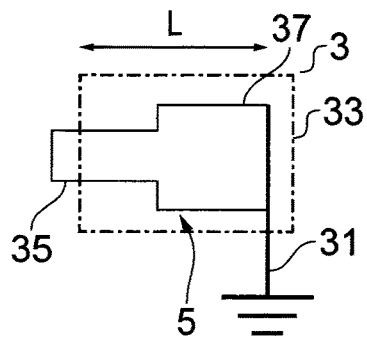

In the examples of FIGS. 3C and 3D the sensitivity of the sensor element 3 is controlled by controlling the combine length L of the sensor material 5 and channel 35 from the conductive portion 31 which is covered by the barrier layer 33. The sensor element 3 of FIG. 3C has a long channel 35 outside of the barrier layer 33 and the sensor element 3 of FIG. 3D has a short channel 35 outside of the barrier layer 33. Only two different exposed channel lengths are shown in FIGS. 3C and 3D however it is to be appreciated that any number of different exposed channel lengths may be used in examples of the disclosure.

In the examples of FIGS. 3C and 3D the different channel lengths are achieved by controlling the length L of the barrier layer 33. This controls the amount of the channel 35 which is covered by the barrier layer 33. In the examples of FIGS. 3C and 3D the sensor material 5 has the same size and shape but the size of the barrier layer 33 is different to change the distance to ground L of the nearest section of exposed channel 35. This may make it simple to manufacture the individual sensor elements 3 using methods such as roll to roll printing or any other suitable method.

In the examples of FIGS. 3A and 3D where the sensing material 5 comprises graphene oxide decreasing the length of the channel 35 which is exposed increases the length of the channel 35 which is not exposed. This increases the time taken for the reduction of the graphene oxide to reach the portion 37 of the sensing material 5 which is adjacent to the conductor 31. In such examples the sensing elements 3 with the shorter exposed channel 35 lengths would be actuated after a higher level of exposure to the parameters.

In each of the examples of FIGS. 3A to 3D different distances to ground from the exposed areas of the channel 35 are provided. However in each of the examples the portion 37 of the sensor material 5 which is adjacent to the conductor 31 may be the same size and shape. In other examples different sizes and shapes of sensor materials 5 may be used.

FIGS. 4A to 4D schematically illustrate some more example sensor elements 3 which may be used in example apparatus 1. In the examples of FIGS. 4A to 4D the sensor elements 3 also comprise a portion of sensing material 5 and a conductive portion 31 connected to ground, and a barrier layer 31 similar to the sensor elements 3 of FIGS. 3A to 3D.

In the examples of FIGS. 4A to 4D a getter material 41 is added to the channels 35. The getter material 41 may be configured to allow for an accurate control of the sensitivity of the sensing elements 3.

Figure 4A:
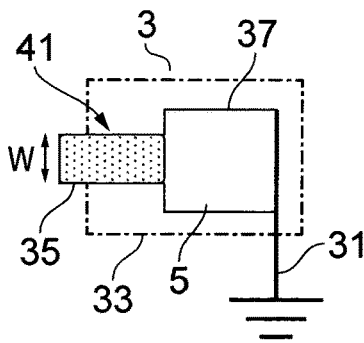
FIGS. 4A to 4D illustrate example sensor elements.
Figure 4C:
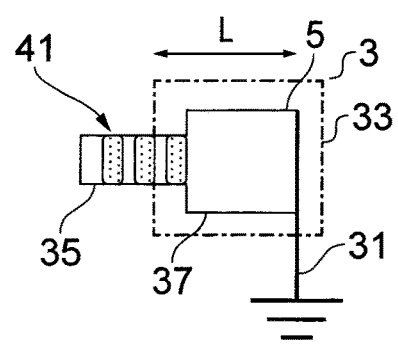
Figure 4B:
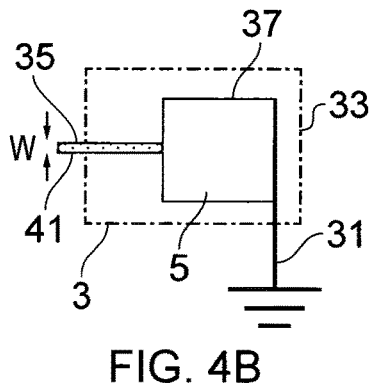

In the examples of FIGS. 4A and 4B the channel 35 of the sensing material 5 is replaced with a channel 35 of getter material. The getter material 41 may allow for a more accurate control of providing the parameter to the sensing material 5 adjacent to the conductor 31. The same getter material 41 may be used in each of the examples of FIGS. 4A and 4B.

The sensor element 3 of FIG. 4A has a wide channel 35 of getter material 41 and the sensor element 3 of FIG. 4B has a narrow channel 35 of getter material 41. Only two different channel widths are shown in FIGS. 4A and 4B however it is to be appreciated that any number of different channel widths may be used in examples of the disclosure.

In examples where the sensing material 5 comprises graphene oxide decreasing the width of the channel 35 of the getter material 41 may increase the time taken for the reduction of the graphene oxide to reach the sensing material 5 in electrical contact with the conductor 31. In such examples the sensing elements 3 with the narrow channel 35 widths would be actuated after a higher level of exposure to the parameters.

Figure 4D:
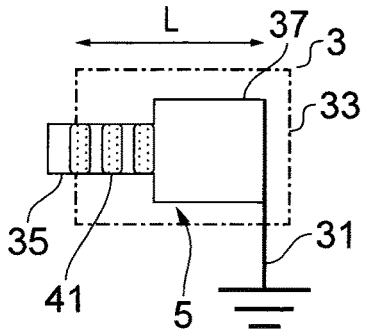

In the examples of FIGS. 4C and 4D the channel 35 of the sensing material 5 comprises strips of getter material 41. The strips of getter material 41 may be printed onto the channel 35 before the sensing material 5. The getter material 41 may allow for a more accurate control of the start point of the reduction of the sensing material 5 within the channel 35 and may enable different lengths of channels 35 to be used.

Figure 5A:
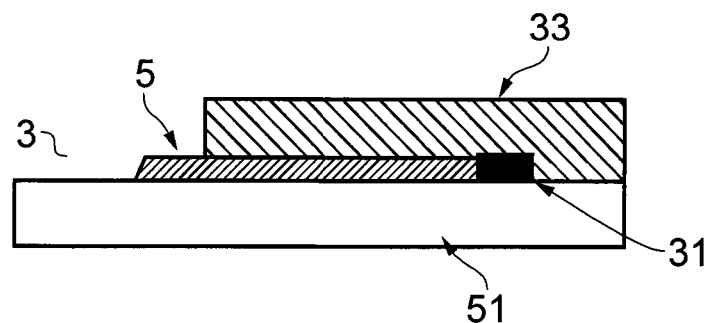
FIGS. 5A and 5B illustrate example sensor elements.
Figure 5B:
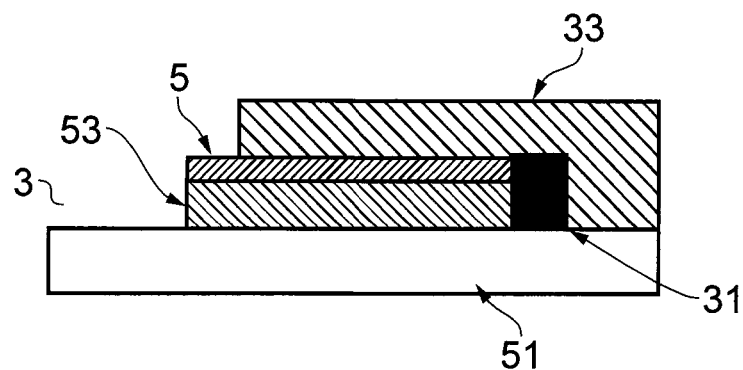

FIGS. 5A and 5B illustrate cross sections through example sensor elements 3. The sensor elements 3 of FIG. 5A and 5B may be sensor elements 3 as schematically illustrated in any of FIGS. 3A to 4D.

The sensor elements 3 comprise a portion of sensing material 5 and a conductor connected to ground 31. The portion of sensing material 5 comprises a channel 35 and a portion 37 adjacent to the conductor 31. The barrier layer 33 is provided overlaying the conductor 31 and the portion 37 of the sensing material 5 adjacent to the conductor 31. A portion of the channel 35 is provided outside of the barrier layer 33 so that it may be exposed to the parameters.

In the examples of FIGS. 5A and 5B the sensor elements may be mounted on a substrate 51. The substrate 51 may comprise any suitable material which allows the sensor elements 3 to be printed upon it.

In the example of FIG. 5A the sensor material 5 may be printed directly on the substrate 51. This may provide a simple manufacturing process. This may ensure that the apparatus 1 has minimal thickness.

In the example of FIG. 5B a porous layer 53 is provided between the substrate 51 and the sensor material 51. The porous layer 53 may be printed on to the substrate 51 before the sensing material 5 and the rest of the sensor element 3 is printed. The porous material 53 may be permeable to the parameter which is to be detected and so may reduce the level of exposure which is needed to actuate the sensor element 3.

Figures 6A, 6B, 6C:
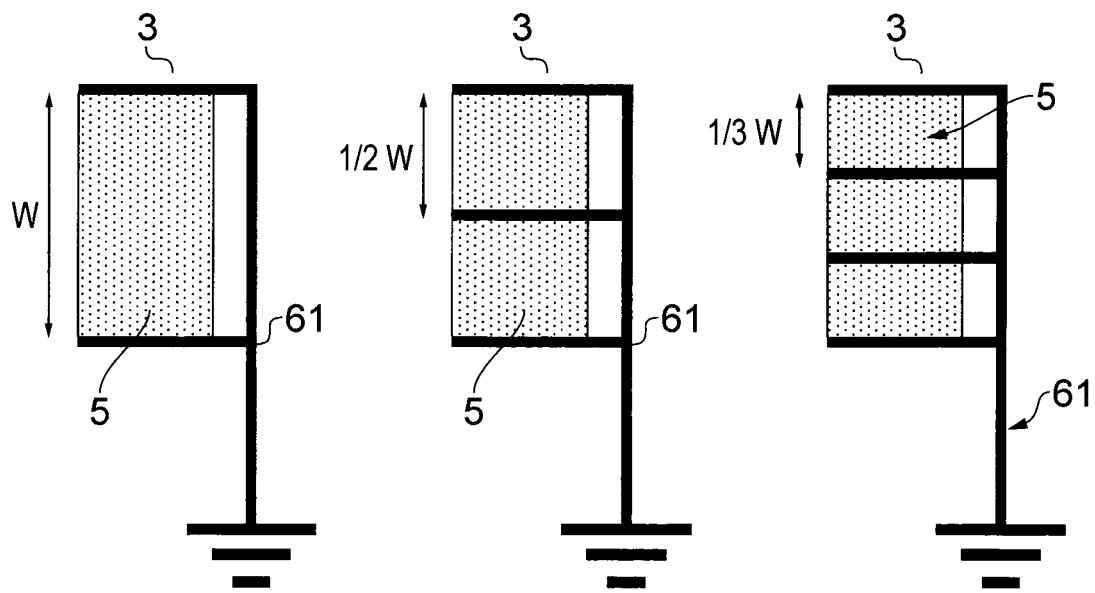
FIGS. 6A to 6C illustrate example sensor elements.

FIGS. 6A to 6C schematically illustrate example sensor elements 3. In the examples of FIGS. 6A to 6C the sensitivity of the sensor elements 3 is adjusted by using different architectures for the conductive electrodes 61.

The examples of FIGS. 6A to 6C comprise single node sensor elements 3. The sensor elements 3 may comprise a portion of graphene oxide as the sensing material 5. Other sensing materials 5 may be used in other examples of the disclosure.

The sensing material 5 may be positioned adjacent to the electrodes 61. When the electrical properties of the sensing material 5 changes this can be detected by applying an electric signal to the sensing element 3. The electric signal may be applied by a capacitive touch screen 23 as described above. For instance, if the sensing material 5 comprises graphene oxide, the graphene oxide becomes reduced graphene oxide and increases in conductivity when exposed to parameters such as increased temperature and humidity. The sensing element 3 then becomes a conductive portion which may be detected by a capacitive touch screen 23.

In each of the sensor elements 3 in FIGS. 6A to 6C the portion of sensing material 5 which is printed is the same size and shape. However, in each of the sensor elements 3 illustrated in FIGS. 6A to 6C the number and spacing of the electrodes 61 is different. In the example of FIG. 6A the spacing between the two electrodes is w which is the whole length of the printed portion of sensing material 5. In the example of FIG. 6B the spacing between the two electrodes is w/2 which is half of the whole length of the printed portion of sensing material 5. In the example of FIG. 6C the spacing between the two electrodes is w/3 which is a third of the whole length of the printed portion of sensing material 5.

This provides a different spacing of sensing material between the conductive electrodes 61. The different spacing of sensing material 5 between electrodes 61 means that each sensing element 3 is actuated in response to a different level of exposure to a parameter. In examples where the sensing material comprises graphene oxide, decreasing the distance of any section of the graphene oxide to the ground electrode 61 reduces the resistance of the path for charge from the graphene oxide to ground. This changes the sensitivity of the sensor element 3.

This design of the example sensor elements 3 of FIGS. 6A to 6C provides the advantage that the layer of sensing material can be deposited in a single print stroke at the same thickness. The portion of sensing material 5 which is printed may be the same size and shape for each sensor element 3. This may make it simple to make a plurality of different sensing elements 3 using printing techniques or any other suitable method.

These sensor elements 3 may also provide the advantage that in some examples only two layers, the sensing material 5 and the conductors 61, may be required to be printed.

Figures 7A, 7B:
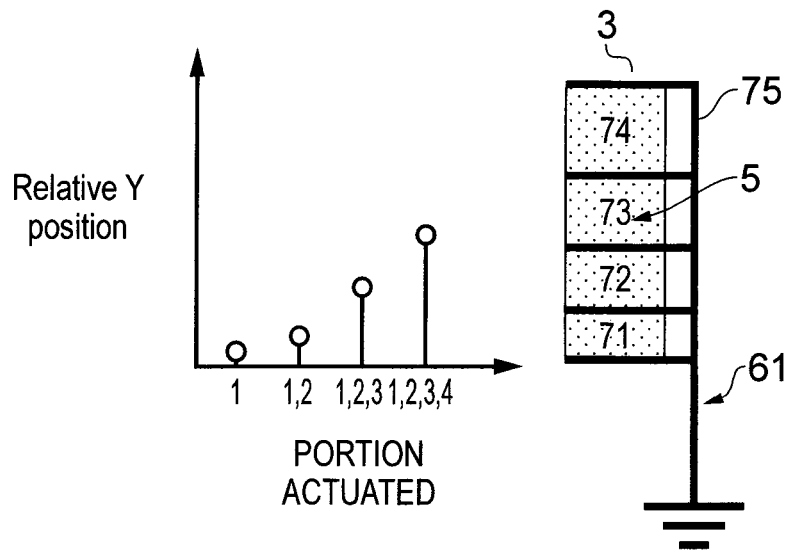
FIGS. 7A and 7B illustrate example sensor elements and example data obtained by a touch screen.

FIGS. 7A and 7B illustrate example sensor elements 3 and example data obtained from the sensor elements 3 by a capacitive touch screen 23.

FIG. 7A schematically illustrates a plurality of sensor elements 3 which are provided in a single node 75. The node 75 of FIG. 7A comprises a sensor material 5 such as graphene oxide. The node 75 also comprises a plurality of electrodes 61 which are each connected to ground. Each of the electrodes 61 are positioned adjacent to a portion of the sensing material 5. Each portion of sensing material 5 and the adjacent electrode 61 provides a different sensor element 3. This arrangement allows a plurality of different sensor elements 3 to be printed in small number of steps.

The electrodes 61 are arranged so that each of the portions of the sensing material 5 may have a different width. The width may define the distance between the electrodes 61. In the example of FIG. 7A the narrowest portion 71 of the sensing material would be actuated first and the widest portion 74 of sensing material 5 would be actuated last.

In the example of FIG. 7A four portions 71, 72, 73, 74 of sensing material are provided. Each portion 71, 72, 73, 74 has a different width. The first portion 71 of the sensing material 5 is the narrowest portion. This is provided at the lower edge of the node 75. The second portion 72 of the sensing material 5 is wider than the first portion 71. The second portion 72 provided next to the first portion in the node 75. The third portion 73 is provided next to the second portion 72. The third portion 73 is wider than both the first portion 71 and the second portion 71. The fourth portion 74 is provided next to the third portion 73 and provides the upper edge of the node 75. The fourth portion 74 is wider than the first portion 71, the second portion 72 and the third portion 73. As each of the sensing elements 3 within the node 75 have different widths they are activated after different levels of exposure to a parameter.

In some examples of the disclosure each of the portions of the sensing material 5 may have a different thickness. The thickness may define the vertical layer thickness of the sensing material 5 between the electrodes 61. In such examples the thickest portion of the sensing material 5 would have the highest conductivity and so would be activated first. The thinnest portion of the sensing material 5 would have the lowest conductivity and so would be activated last. As each of the portions of the sensing material 5 have different conductivity they are activated after different levels of exposure to a parameter.

FIG. 7B shows data which may be obtained by a capacitive touch screen 23 when the sensing elements 3 of the node 75 are activated. The capacitive touch screen 23 may be configured to detect the conductive portions 71, 72, 73, 74 of the sensing material 5. FIG. 7B shows the relative y position of the detected touch event as the apparatus 1 is exposed to a higher level of the parameter and/or is exposed for a longer period of time. In the example of FIGS. 7A and 7B portion 71 is actuated first. This causes the capacitive touch screen 23 to detect a conductive portion at a first position on the y axis as indicated in FIG. 7B.

After the apparatus 1 is exposed to a parameter for a longer period of time portions 71 and 72 become actuated. This creates two conductive portions in the node 75 and the effective position of the conductive portion detected by the capacitive touch screen 23 moves upwards on the y axis.

After the apparatus 1 is exposed to a parameter for a further period of time portion 73 becomes actuated. This creates three conductive portions in the node 75 and the effective position of the conductive portion moves upwards on the y axis. When the apparatus 1 has been exposed for even longer then portion 74 becomes actuated as well and this causes the effective position of the conductive portion to move further up the y axis again.

In some examples the apparatus 1 may comprise one or more reference electrodes. The reference electrodes may be used to enable the position of the conductive portions to be determined by comparing the position of the detected conductive portions to the position of the reference electrodes. In some examples three reference electrodes may be provided. These may be provided in three of the corners of the apparatus 1.

The example sensor elements of FIGS. 7A and 7B provide the advantage that a plurality of sensing elements 3 can be detected by a single touch input on a capacitive touch screen 23. This may be useful in examples where the number of touch inputs that the capacitive touch screen 23 can detect simultaneously is limited. For example, capacitive touch screens 23 may only be able to detect ten simultaneous touch inputs.

Figures 8A, 8B:
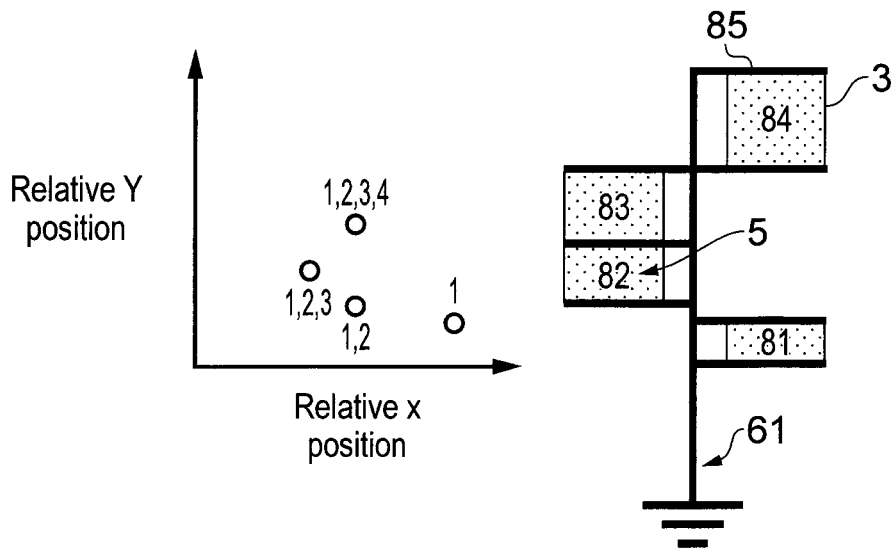
FIGS. 8A and 8B illustrate example sensor elements and example data obtained by a touch screen.

FIGS. 8A and 8B illustrate example sensor elements 3 and example data obtained by a capacitive touch screen 23. The plurality of sensor elements 3 illustrated in FIG. 8A are similar to those of FIG. 7A in that they comprise a plurality of different portions of sensing material 5 provided in a single node 85. Each of the different portions of sensing material 5 has a different width so that each sensing element 3 has a different sensitivity. Each of the different portions of sensing material 5 is connected to an electrode 61 which is connected to ground However in FIG. 7A each of the sensing elements 3 are provided in the same x position whereas in the node 85 of FIG. 8A some of the sensing elements 3 have different x positions. This causes the detected position of the conductive portions to change the x position as well as the y position as the different sensing elements 3 are actuated and detected by a capacitive touch screen 23.

In the example of FIG. 8A four portions 81, 82, 83, 84 of sensing material are provided. Each portion 81, 82, 83, 84 has a different width. The first portion 81 of the sensing material 5 is the narrowest portion. This is provided at the lower edge of the node 85 and on the right hand side of the connection to ground. The second portion 82 of the sensing material 5 is wider than the first portion 81. The second portion 82 provided above the first portion in the node 85 but on the left hand side of the connection to ground. The third portion 83 is provided next to the second portion 82. The third portion 83 is wider than both the first portion 81 and the second portion 81. The third portion is also provided on the left hand side of the connection to ground. The fourth portion 84 is provided above the third portion 83. The fourth portion 84 is wider than the first portion 81, the second portion 82 and the third portion 83. The fourth portion is provided on the right hand side of the connection to ground. It is to be appreciated that other numbers or sensing elements 3 and arrangements of sensing elements 3 may be used in other examples of the disclosure.

In some examples of the disclosure each of the portions of the sensing material 5 may have a different thickness. The thickness may define the vertical layer thickness of the sensing material 5 between the electrodes 61. In such examples the thickest portion of the sensing material 5 would have the highest conductivity and so would be activated first. The thinnest portion of the sensing material 5 would have the lowest conductivity and so would be activated last. As each of the portions of the sensing material 5 have different conductivity they are activated after different levels of exposure to a parameter.

FIG. 8B shows data which may be obtained by a capacitive touch screen 23 when the sensing elements 3 of the node 85 are activated. The capacitive touch screen 23 may be configured to detect the conductive portions 81, 82, 83, 84 of the sensing material 5. FIG. 8B shows the relative x and y positions of the detected touch event as the apparatus 1 is exposed to a higher level of the parameter. In the example of FIGS. 8A and 8B portion 81 is activated first. This causes the capacitive touch screen 23 to detect a conductive portion at a first position on the x and y axis as indicated in FIG. 8B.

After the apparatus 1 is exposed to a parameter for a longer period of time portions 81 and 82 become actuated. This creates two conductive portions in the node 85 and the effective position of the conductive portion detected by the capacitive touch screen 23 moves upwards on the y axis and towards the left on the x axis.

After the apparatus 1 is exposed to a parameter for a further period of time portion 83 becomes actuated. This creates three conductive portions in the node 85 and the effective position of the conductive portion moves upwards on the y axis and further to the left on the x axis. When the apparatus 1 has been exposed for even longer then portion 84 becomes actuated as well and this causes the effective position of the conductive portion to move further up the y axis but back towards the right on the x axis.

Figure 9:
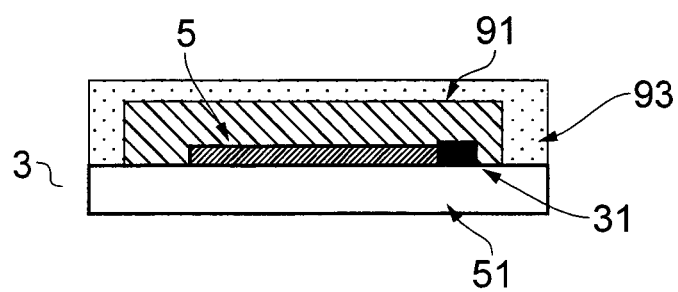
FIG. 9 illustrates an example sensor element.

FIG. 9 illustrates an example sensor element 3 which may be used to detect exposure to a parameter such as UV light. The sensor element 3 comprises a portion of sensing material 5 and a conductor 31 which may be printed on a substrate 51. The sensing material 5, conductor 31 and substrate 51 may be as described above in reference to any of the previous examples.

The sensor element 3 comprises a first barrier layer 91. The first barrier layer 91 may be configured to be impermeable to moisture or other parameter. In some examples the first barrier layer 91 may fully encapsulate the sensing material 5. This may prevent the sensor element 3 from being actuated by moisture or a parameter other than UV light.

The example sensor element 3 of FIG. 9 also comprises a second barrier layer 93. The second barrier layer 93 may be provided overlaying the first barrier layer 91. The second barrier layer 93 may completely encapsulate the sensing material and the first barrier layer 91.

In the example of FIG. 9 the second barrier layer 93 may be configured to control the amount of UV light which reaches the sensing material 5. The second barrier layer 93 may comprise a material which may be configured to absorb UV light. For example, the second barrier layer 93 may comprise zinc oxide, titanium dioxide, or any other suitable material.

In some examples the apparatus 1 may comprise a plurality of sensor elements 3 as illustrated in FIG. 9. Each of the sensor elements 3 may be configured to have a different sensitivity to UV light. The sensitivity of each sensor element 3 to UV light may be controlled by controlling the permeability of the second barrier layer 93 to UV light. The permeability of the second barrier layer may be controlled by changing the thickness of the barrier layer and/or the materials within the barrier layer 93 or by any other suitable means.

The example sensor element 3 of FIG. 9 is suitable for use where only a single parameter needs to be detected. In the example of FIG. 9 the sensor element 3 is configured to detect UV light. In other examples the sensor element 3 may be configured to detect other parameters by choosing appropriate materials for the barrier layers 91, 93.

Figure 10A:
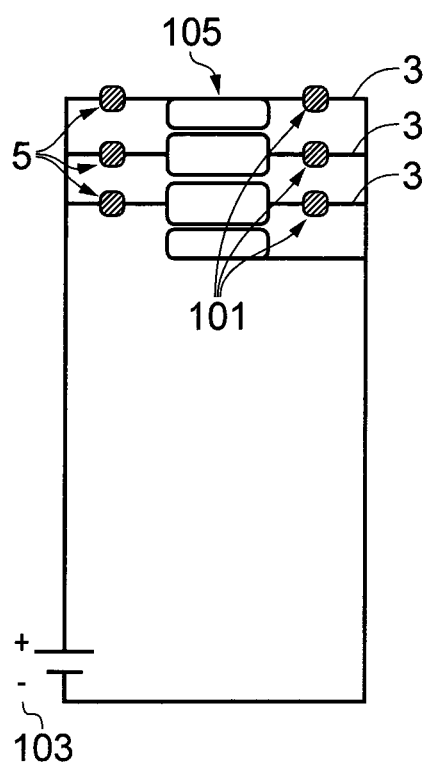
FIGS. 10A and 10B illustrate example sensor elements.
Figure 10B:
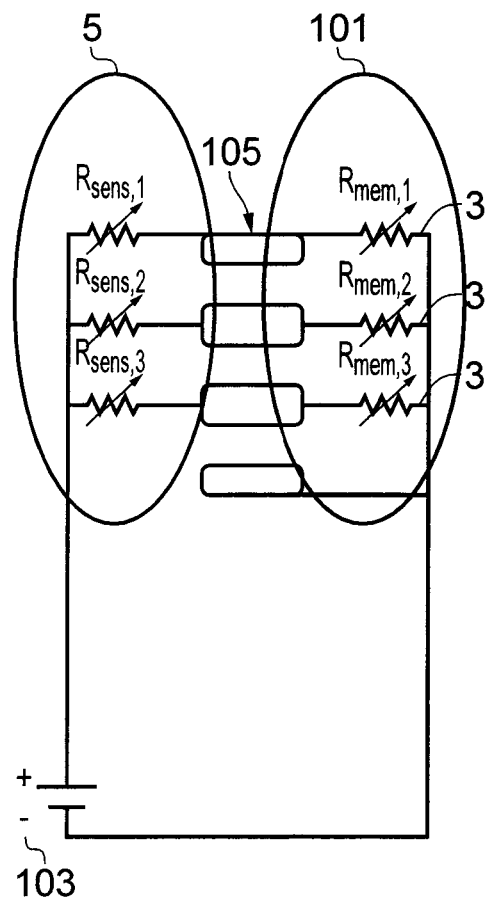

FIGS. 10A and 10B illustrate example sensor elements 3 according to another example of the disclosure. FIG. 10A shows an example configuration for combining portions of sensing material 5 with irreversible memory elements 101. FIG. 10B shows the equivalent circuit components. Each of the sensor elements 3 of FIGS. 10A and 10B comprise a portion of sensing material 5 coupled to an irreversible memory element 101.

In the examples of FIGS. 10A and 10B a power source 103 may be provided within the apparatus 1. The power source 103 may comprise any means which is suitable for providing power to example sensor elements 3. For example the power source 103 may comprise one or more batteries, a supercapacitor, an energy harvesting element or any other suitable means.

In the example of FIGS. 10A and 10B the sensing material 5 may be configured to undergo a reversible change in response to exposure to a parameter. For example the sensing material 5 may comprise graphene oxide which may be configured to undergo a reversible reduction when exposed to low levels of humidity.

The memory element 101 may comprise means which may be configured to undergo an irreversible change when the sensor material 5 detects a threshold level of a parameter. This enables the apparatus 1 to integrate the exposure level of the sensor elements 3 over time.

In the examples of FIGS. 10A and 10B the memory elements 101 are coupled to the sensing material 5 via a capacitive electrode 105. The sensing material 5 and the memory elements are coupled to the power source 103. When the sensing material 5 is exposed to a parameter this will cause the resistance of the sensing material 5 to decrease. For example if graphene oxide is exposed to humidity this causes the graphene oxide to become reduced graphene oxide and increase in conductivity. When the parameter sensed by the sensing material 5 exceeds a given threshold value the decrease in the resistance of the sensor element 3 causes the voltage to become coupled over the irreversible memory element 101. The resistance of the memory element 101 decreases by an amount proportional to the resistance of the sensing material 5. The decrease in the resistance of the memory element 101 may be caused by joule heating effects which may be irreversible.

Once the resistance of the memory element 101 is low enough, the capacitive electrode which couples the memory element 101 to the sensing material 5 will become coupled to the ground. This change may be detected through any suitable means such as a capacitive touch screen 23.

In the examples of FIGS. 10A and 10B three sensor elements 3 are provided. It is to be appreciated that other numbers of sensor elements 3 may be provided in other examples of the disclosure.

In some examples the apparatus 1 may comprise a plurality of sensor elements 3 as illustrated in FIGS. 10A and 10B. In some examples the portion 5 of sensing material may be identical for each of the sensor elements 3. However the memory element 101 may be different. For instance the volume of material within each of the memory elements 101 may be different. This may cause the memory elements 101 to be triggered in response to different threshold levels of a parameter. This may enable the different sensor elements 3 to be activated when the different memory elements 101 are triggered.

Figure 11:
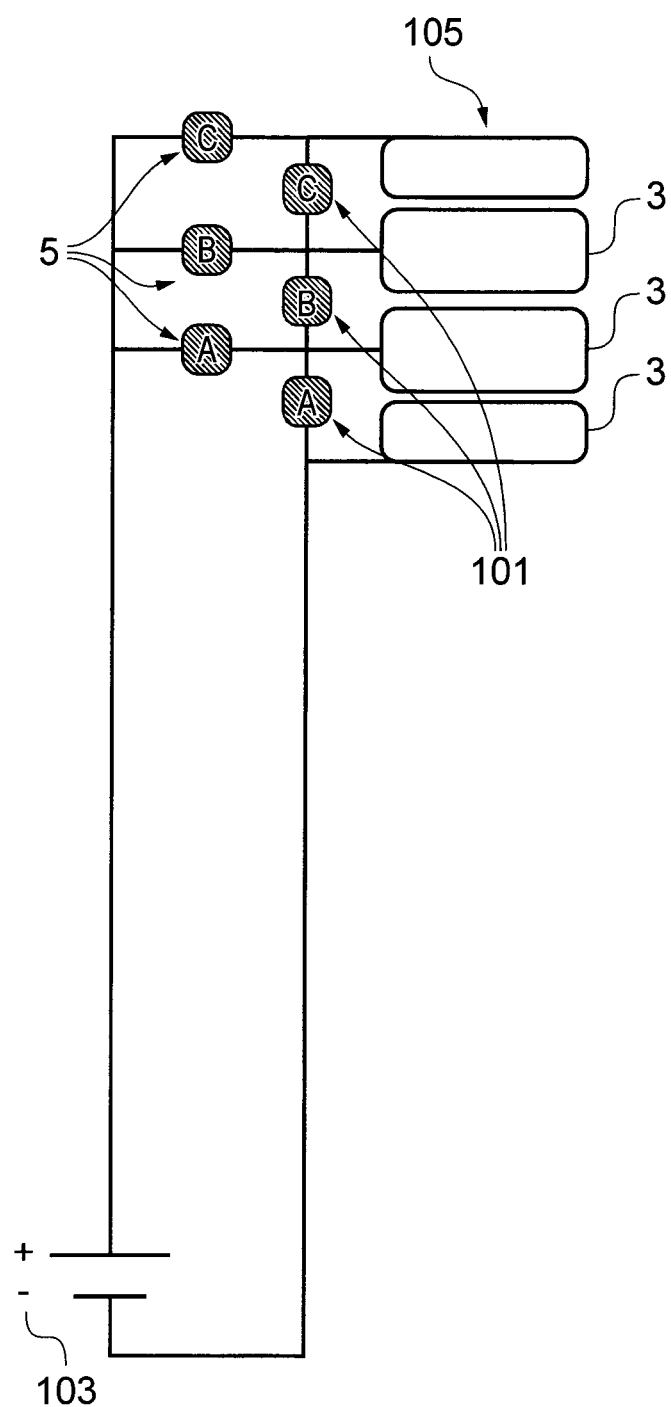
FIG. 11 illustrates an array of example sensor elements.

FIG. 11 illustrates an another example of a plurality of sensor elements 3 which may comprise portions of sensing material 5 and irreversible memory elements 101. Each of the memory elements 101 is connected to a capacitive electrode 105 so that the decrease in resistance of the memory element 101 connects the capacitive electrodes 105 to ground. Actuation of the sensor elements 3 may be detected using means such as a capacitive touch screen 23 which can determine which of capacitive electrodes 105 are coupled to ground.

The example configuration of FIG. 11 may be used when each of the portions of sensing material 5 have a different level of sensitivity. Any suitable means may be used to provide the sensing materials 5 with different levels of sensitivity. For instance, some of the examples described above may be used to control the sensitivity of the sensing material 5.

As the portions of sensing material 5 have different sensitivities the most sensitive portion of sensing material 5 will decrease in resistance before the others. In the example of FIG. 11 the lowest portion of sensing material 5A is the most sensitive. This will cause the lowest memory element 101A to decrease in resistance first.

The middle portion of sensing material 5B is the next most sensitive. This will cause the middle memory element 101A to activated next. The top portion of sensing material 5C is the next most sensitive portion. When this is conductive this will cause the top memory element 101C to be actuated.

Figure 12:
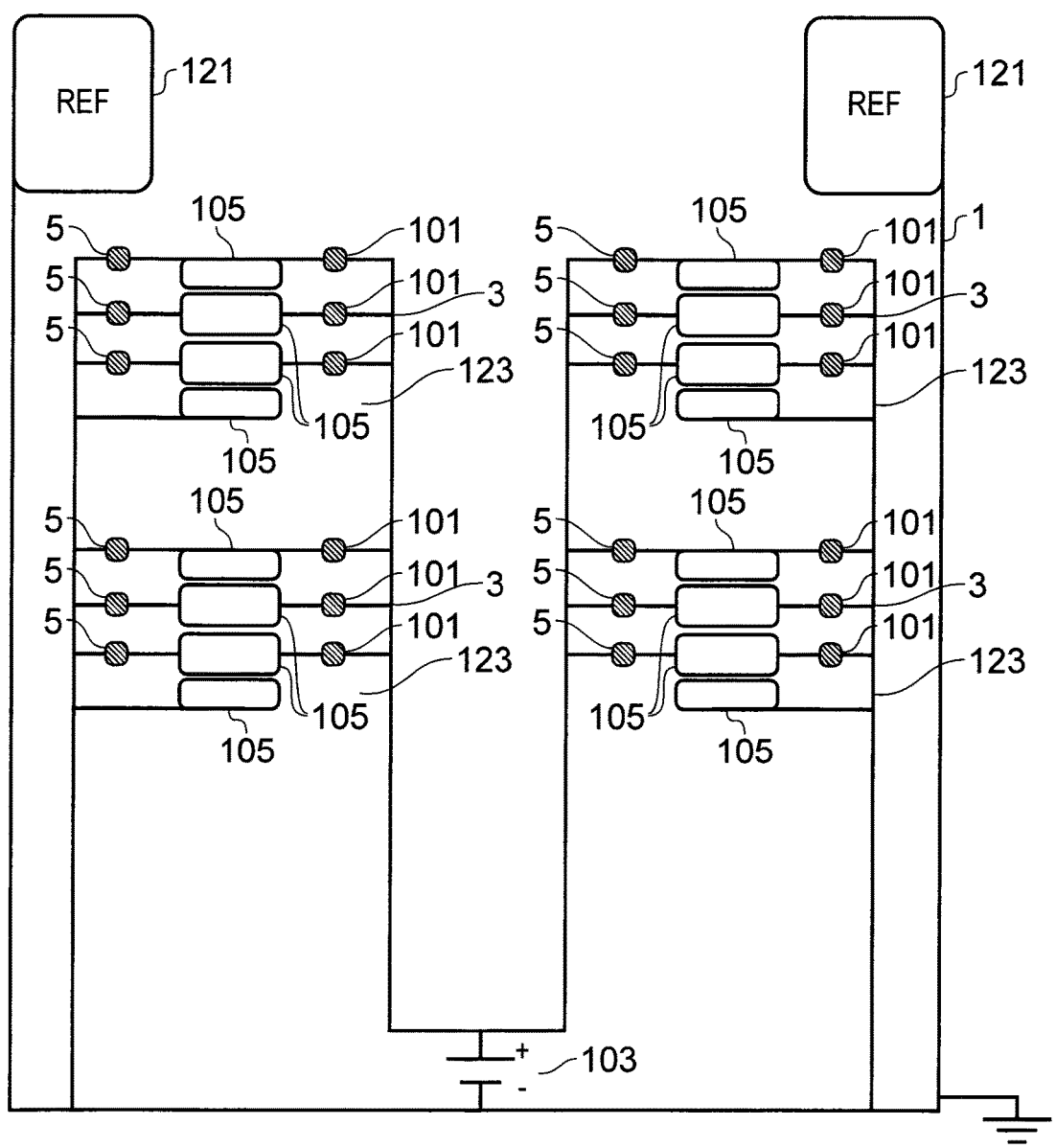
FIG. 12 illustrates an array of example sensor elements.

FIG. 12 illustrates an array of sensor elements 3 which may be provided in an example apparatus 1 as described above. The example apparatus 1 of FIG. 12 comprises a plurality of sensor elements 3. The sensor elements 3 comprise a portion of sensing material 5 and an irreversible memory element 101 as described above. In FIG. 12 the sensor elements 3 comprise sensing material 5 which is coupled to the irreversible memory element 101 via a capacitive electrode 105 as illustrated in FIGS. 10A and 10B and described above. It is to be appreciated that other configurations may be used in other examples.

The example apparatus 1 of FIG. 12 comprises reference electrodes 121. The reference electrodes may enable a capacitive touch screen 23 to determine the positions of the actuated sensor elements 3. In the example of FIG. 12 two reference electrodes 121 are provided. It is to be appreciated that other numbers of reference electrodes may be provided in other examples.

The reference electrodes 121 are electrically connected to ground. The reference electrodes may be electrically connected to ground so that a path for direct current is provided between the reference electrodes 121 and ground. The capacitive electrodes 105 are also electrically connected to the ground.

The electrodes 105, 121 can only be detected by the capacitive touch screen 23 if they have a sufficient ground. In some examples the electrodes 105, 121 may need to be activated by an electrical connection to a charge reservoir such as a finger of a user.

The reference electrodes 121 may always be electrically connected to the ground. The reference electrodes 121 may be used to detect when the apparatus 1 is activated by a finger or other charge reservoir being placed on the capacitive touch screen 23. The reference electrodes 121 may also be used to ensure that the apparatus 1 is correctly laid on the surface of the capacitive touch screen 23.

In the example of FIG. 12 two reference electrodes 121 and a ground are provided. These provide three points which define a plane which enables the capacitive touch screen 23 to determine that the apparatus 1 is correctly positioned relative to the capacitive touch screen 23.

The reference electrodes 121 may also be configured to enable the apparatus 1 to be orientated in any direction on the capacitive touch screen 23 as the position of the capacitive electrodes 105 can be taken relative to the reference electrodes 121. The relative position of the reference electrodes 121 could also be used to identify any relative position change between the apparatus 1 and the capacitive touch screen 23 which may occur in activating the different sensor elements 3. It is to be appreciated that reference electrodes may be provided in other examples such as those described with reference to FIGS. 6 to 9.

The sensor elements 3 may be configured to enable different parameters to be measured. For example the apparatus 1 of FIGS. 12 comprises four groups 123 of sensor elements 3. Each of the different groups 123 of sensor elements 3 may be configured to detect different parameters or combinations of parameters. In some examples one or more the groups 123 of sensor elements 3 may be configured to detect the same parameters. In such examples the groups 123 may be configured to have different sensitivities to the same parameters.

Figure 13:
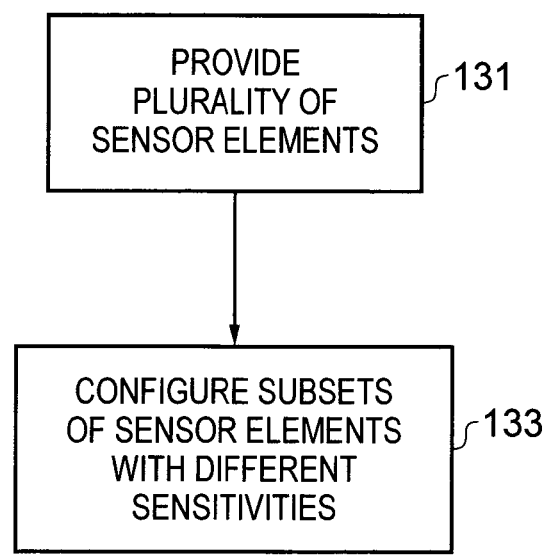
FIG. 13 illustrates an example method.

FIG. 13 illustrates an example method. The method comprises providing, at block 131, a plurality of sensor elements 3 on an apparatus 1 wherein the sensor elements 3 are configured to be actuated in response to exposure to a parameter and the apparatus 1 is configured to record when each of the sensor elements 3 are actuated. At block 133 the method comprises configuring subsets of sensor elements 3 with different sensitivities. The method may comprise configuring the plurality of sensor elements 3 such that at least a first subset of sensor elements 3 are actuated in response to a first level of exposure to a parameter and at least a second subset of sensor elements 3 are actuated in response to a second level of exposure to a parameter.

The sensor elements 3 may be formed using any suitable methods. For example the sensor elements 3 may be formed by creating regions of sensor material 5 such as graphene oxide on a substrate 51. The substrate 51 may comprise any suitable material such as Polyethylene terephthalate (PET).

In some examples the apparatus 1 may be formed by depositing a Fluoropolymer mask onto a substrate by flexographic printing. The mask may be configured to direct graphene oxide solution into hydrophilic shapes. The graphene oxide, or other sensor material 5 may be coated onto the substrate using any suitable means. For example, a solution of graphene oxide may be coated in to a substrate by slot die, air knife, meter bar, slide hopper or any other suitable means.

It is to be appreciated that any other suitable patterning method may be used such as screen printing, rotary screen printing, inkjet printing, flexographic printing, gravure printing, spray coating, pad printing, intaglio printing or any other method.

The example apparatus 1 and methods described above addresses a number of technical problems. The example apparatus 1 may be provided at an extremely low-cost as it does not require any processing components or any moving parts. The example apparatus 1 may be manufactured using processes such as roll to roll processing which may allow a large number of apparatus to be manufactured. This makes the apparatus suitable for use on large numbers or goods.

Furthermore, the apparatus 1 may be configured so that the data obtained by the apparatus 1 can be read by using a capacitive touch-screen 23. The capacitive touch screen 23 may be provided on a device such as a user's phone or tablet computer. This enables more detailed data to be obtained compared to a sensor which only provides a visual indication of the parameter history.

Also the apparatus 1 used an array of sensor elements 3 where different sensor elements 3 are actuated at different levels of exposure enables. This enables more detailed information to be obtained relating to the history of the environment the apparatus 1 has been exposed to. For example, if only the most sensitive sensor element 3 has been actuated then the exposure level of the apparatus 1 is quite low. If a larger number of the sensor elements have been actuated then the exposure level is higher. The number of actuated sensor elements 3 may be used to provide a detailed history of the parameters such as temperature, humidity and UV light which the apparatus 1 has been exposed to.

The apparatus 1 may be extremely thin and light weight. This may make the apparatus easy to add to goods or the packaging of goods. In some examples the apparatus 1 may be patterned directly onto the goods or the packaging of the goods.

The sensor elements 3 and apparatus 1 described above are simple structures which can be fabricated by printing. This means that the apparatus may be low cost which may make them suitable for use in supply chains or other areas.

As the data from the sensor elements can be read out using a capacitive touch screen 23 this may enable a greater range of parameters to be detected.

In the examples described above the term coupled means operationally coupled and any number or combination of intervening elements can exist (including no intervening elements).

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising:
    a plurality of sensor elements wherein the sensor elements are configured to be actuated in response to exposure to a parameter and the apparatus is configured to record when each of the sensor elements are actuated wherein: the plurality of sensor elements comprises at least a first subset of one or more sensor elements and at least a second subset of one or more sensor elements where the first subset of one or more sensor elements is actuated in response to a first level of exposure to a parameter and the second subset of one or more sensor elements is actuated in response to a second level of exposure to a parameter,
    wherein at least one of the plurality of sensor elements comprise a portion of sensing material and an irreversible memory portion, wherein the portion of sensing material and the irreversible memory portion are connected in a circuit;
    wherein the plurality of sensor elements are arranged such that when the exposure to the parameter sensed by the sensing material exceeds a threshold value, a reversible change in conductivity of the sensing material caused by the exposure to the parameter causes an irreversible change in an electrical characteristic of the irreversible memory portion, thereby causing an irreversible change in an electrical characteristic in the circuit.

2. An apparatus as claimed in claim 1 wherein the plurality of sensor elements are configured so that the sensing material within the first subset of one or more sensor elements is configured to detect a first level of exposure to a parameter and the sensing material within the second subset of one or more sensor elements is configured to detect a second level of exposure to a parameter.

3. An apparatus as claimed in claim 1 wherein the sensing material comprises graphene oxide wherein the graphene oxide is configured to be reduced in response to exposure to a parameter.

4. An apparatus as claimed in claim 1 wherein the first subset of sensing elements comprise the sensing material having a first width and the second subset of sensing elements comprise the sensing material having a second width.

5. An apparatus as claimed in claim 1 wherein the first subset of sensing elements comprise a first barrier layer with a first level of permeability to the parameter and the second subset of sensing elements comprise a second barrier layer with a second level of permeability to the parameter.

6. An apparatus as claimed in claim 1 wherein the plurality of sensing elements comprise a getter material configured to control the sensitivity of the sensor elements to the parameter.

7. An apparatus as claimed in claim 1 wherein each of the portions of sensing material are identical but each of the irreversible memory portions are different.

8. An apparatus as claimed in claim 1 wherein the plurality of sensor elements comprise electrodes to enable the data obtained by the sensor elements to be read out from the apparatus using a capacitive device.

9. An apparatus as claimed in claim 8 comprising at least one reference electrode configured to enable relative positions of sensor elements to be determined, wherein the sensor elements have differing levels of sensitivity such that the relative position of an activated sensor element indicates a relative level of exposure to a parameter.

10. An apparatus as claimed in claim 8 wherein the apparatus is configured to enable data read out from the apparatus to be displayed on the capacitive device.

11. An apparatus as claimed in claim 1 wherein the sensor elements are configured to be activated in response to exposure to at least one of increased temperature, light, humidity.

12. An identification tag comprising an apparatus, the apparatus comprising:
- a plurality of sensor elements wherein the sensor elements are configured to be actuated in response to exposure to a parameter and the apparatus is configured to record when each of the sensor elements are actuated wherein:
- the plurality of sensor elements comprises at least a first subset of one or more sensor elements and at least a second subset of one or more sensor elements where the first subset of one or more sensor elements is actuated in response to a first level of exposure to a parameter and the second subset of one or more sensor elements is actuated in response to a second level of exposure to a parameter,
- wherein at least one of the plurality of sensor elements comprise a portion of sensing material and an irreversible memory portion, wherein the portion of sensing material and the irreversible memory portion are connected in a circuit,
- wherein the plurality of sensor elements are arranged such that when the exposure to the parameter sensed by the sensing material exceeds a threshold value, a reversible change in conductivity of the sensing material caused by the exposure to the parameter causes an irreversible change in an electrical characteristic of the irreversible memory portion, thereby causing an irreversible change in an electrical characteristic in the circuit.

13. An identification tag as claimed in claim 12 wherein the plurality of sensor elements are configured so that the sensing material within the first subset of one or more sensor elements is configured to detect a first level of exposure to a parameter and the sensing material within the second subset of one or more sensor elements is configured to detect a second level of exposure to a parameter.

14. An identification tag as claimed in claim 12 wherein the sensing material comprises graphene oxide wherein the graphene oxide is configured to be reduced in response to exposure to a parameter.

15. An identification tag as claimed in claim 12 wherein the first subset of sensing elements comprise the sensing material having a first width and the second subset of sensing elements comprise the sensing material having a second width.

16. An identification tag as claimed in claim 12 wherein the first subset of sensing elements comprise a first barrier layer with a first level of permeability to the parameter and the second subset of sensing elements comprise a second barrier layer with a second level of permeability to the parameter.

17. A method comprising:
- with at least a processor of an electronic device, causing detection of at least one electrical characteristic in a respective circuit of a plurality of circuits, each circuit comprising a respective portion of sensing material coupled to a respective irreversible memory portion;
- wherein each respective portion of sensing material is comprised by a respective sensor element of a plurality of sensor elements, wherein a reversible change to conductivity of a respective portion of sensing material occurs in response to an exposure to at least a threshold of a parameter, thereby causing a respective irreversible change in the electrical characteristic in the respective circuit.

18. A method as claimed in claim 17 wherein the plurality of sensor elements are configured so that the sensing material within a first subset of one or more sensor elements is configured to detect a first level of exposure to the parameter and the sensing material within a second subset of one or more sensor elements is configured to detect a second level of exposure to the parameter.

19. A method as claimed in claim 17 wherein the sensing material comprises graphene oxide, wherein the graphene oxide is configured to be reduced in response to exposure to the parameter.

20. A method as claimed in claim 17 wherein a first subset of sensing elements comprise the sensing material having a first width and a second subset of sensing elements comprise the sensing material having a second width.

* * * * *